United States Patent [19]

Elbe et al.

[11] Patent Number: 5,047,544

[45] Date of Patent: * Sep. 10, 1991

[54] PESTICIDAL SUBSTITUTED PYRIDINE DERIVATIVES

[75] Inventors: Hans-Ludwig Elbe, Wuppertal; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[*] Notice: The portion of the term of this patent subsequent to Jul. 3, 2008 has been disclaimed.

[21] Appl. No.: 456,599

[22] Filed: Dec. 26, 1989

Related U.S. Application Data

[63] Continuation of Ser. No. 226,162, Jul. 29, 1988, abandoned.

[30] Foreign Application Priority Data

Aug. 5, 1987 [DE] Fed. Rep. of Germany ....... 3725967
May 7, 1988 [DE] Fed. Rep. of Germany ....... 3815700

[51] Int. Cl.$^5$ .................. A01N 43/40; C07D 213/30; C07D 213/34
[52] U.S. Cl. .................................. 514/277; 546/339; 546/344
[58] Field of Search .................. 546/344, 339; 514/277

[56] References Cited

FOREIGN PATENT DOCUMENTS

| 15703 | 6/1968 | Australia | 546/344 |
| 0001399 | 4/1979 | European Pat. Off. | 546/344 |
| 0111234 | 6/1984 | European Pat. Off. | 548/341 |
| 0157712 | 10/1985 | European Pat. Off. | 546/344 |
| 0221844 | 5/1987 | European Pat. Off. | 546/315 |

OTHER PUBLICATIONS

Chemical Abstracts, vol. 107(17), Abst. No. 154,243, published Oct. 26, 1987.
Jpn. Kokai Tokyo Koho, JP 62-84061, pp. 1-25, Published Apr. 17, 1987.

*Primary Examiner*—Alan L. Rotman
*Attorney, Agent, or Firm*—Sprung, Horn, Kramer & Woods

[57] ABSTRACT

Fungicidal substituted pyridine derivatives of the formula

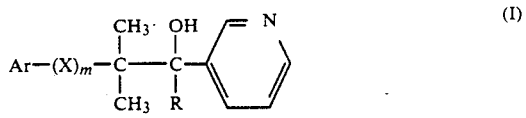

in which
Ar stands for optionally substituted aryl,
X stands for oxygen, sulphur, sulphinyl, sulphonyl or for one of the groups —CH$_2$—; —O—CH$_2$—; —CH$_2$—O—; —O—CH$_2$—CH$_2$—; —S(O)$_n$—CH$_2$—; —CH$_2$—S(O)$_n$— or —S(O)$_n$—CH$_2$—CH$_2$—, in which
n in each case stands for the number 0, 1 or 2,
R stands for alkyl, alkenyl, alkinyl, alkoxyalkyl, alkylthioalkyl, cycloalkyl, cycloalkylalkyl or for in each case optionally substituted aryl, aralkyl, aryloxyalkyl or arylthioalkyl and
m stands for the number 0 or 1, and plant-compatible acid and metal salt addition products thereof. Intermediates of the formula

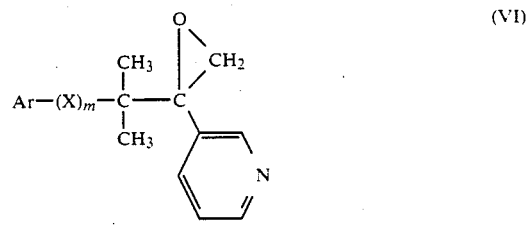

are also new.

9 Claims, No Drawings

PESTICIDAL SUBSTITUTED PYRIDINE DERIVATIVES

This application is a continuation of application Ser. No. 226,162, filed 7/29/88, abandoned.

The invention relates to new substituted pyridine derivatives, several processes for their preparation and also their use as pest-combating agents.

It has already been disclosed that certain substituted pyridine derivatives, such as, for example, 2-(4-chlorophenoxy)-1-(2,4-dichlorophenyl)-1-(3-pyridyl)-ethanol or 1-(4-chloro-2-methyl-phenoxy)-3,3-dimethyl-2-(3-pyridyl)-2-butanol or 3,3-dimethyl-1-(2-methylphenoxy)-2-(3-pyridyl)-2-butanol or 1-(2,4-dichlorophenoxy)-3,3-dimethyl-2-(3-pyridyl)-2-butanol or their plant-compatible acid addition salts such as, for example, their naphthalene-1,5-disulphonates possess fungicidal properties (compare EP 1,399).

However, the activity of these previously known compounds is not completely satisfactory in all areas of application, in particular at low application rates and concentrations.

New substituted pyridine derivatives of the general formula (I)

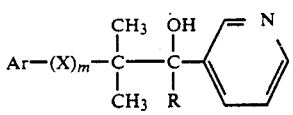

(I)

in which
Ar stands for optionally substituted aryl,
X stands for oxygen, sulphur, sulphinyl, sulphonyl or for one of the groups —CH$_2$—; —O—CH$_2$—; —CH$_2$—O—; —O—CH$_2$—CH$_2$—; —S(O)$_n$—CH$_2$—; —CH$_2$—S(O)$_n$— or —S(O)$_n$—CH$_2$—CH$_2$—,
in which
n in each case stands for the number 0, 1 or 2,
R stands for alkyl, alkenyl, alkinyl, alkoxyalkyl, alkylthioalkyl, cycloalkyl, cycloalkylalkyl or for in each case optionally substituted aryl, aralkyl, aryloxyalkyl or arylthioalkyl and
m stands for the number 0 or 1, and also their plant-compatible acid addition salts and metal salt complexes, have now been found.

The compounds of the formula (I) can exist as geometrical and/or optical isomers or isomer mixtures of different composition. Both the pure isomers and also the isomer mixtures are claimed according to the invention.

Furthermore, it has been found that the new substituted pyridine derivatives of the general formula (I)

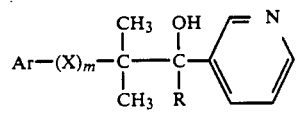

(I)

in which
Ar stands for optionally substituted aryl,
X stands for oxygen, sulphur, sulphinyl, sulphonyl or for one of the groups —CH$_2$—; —O—CH$_2$—; —CH$_2$—O—; —O—CH$_2$—CH$_2$—; —S(O)$_n$—CH$_2$—; —CH$_2$—S(O)$_n$— or —S(O)$_n$—CH$_2$—CH$_2$—,
in which
n in each case stands for the number 0, 1 or 2,
R stands for alkyl, alkenyl, alkinyl, alkoxyalkyl, alkylthioalkyl, cycloalkyl, cycloalkylalkyl or for in each case optionally substituted aryl, aralkyl, aryloxyalkyl or arylthioalkyl and
m stands for the number 0 or 1, and also their plant-compatible acid addition salts and metal salt complexes are obtained, when
(a) ketones of the formula (II)

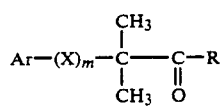

(II)

Ar, X, R and m have the abovementioned meaning, are reacted with pyridyl Grignard compounds of the formula (III)

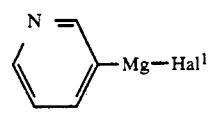

(III)

in which Hal$^1$ stands for halogen, if appropriate in the presence of a diluent or when
(b) pyridyl ketones of the formula (IV)

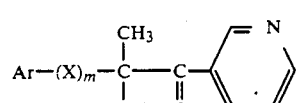

(IV)

in which Ar, X and m have the abovementioned meaning, are reacted with alkyl Grignard compounds of the formula (V)

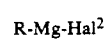

R-Mg-Hal$^2$ (V)

in which
R has the abovementioned meaning and
Hal$^2$ stands for halogen,
if appropriate in the presence of a diluent or also alternatively, when in order to obtain substituted pyridine derivatives of the formula (Ia)

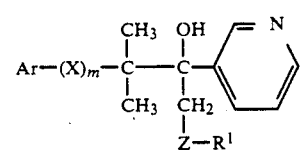

(Ia)

in which
Z stands for oxygen or sulphur,
R$^1$ stands for alkyl or for optionally substituted aryl and
Ar, X and m have the abovementioned meanings,
(c) pyridyl oxiranes of the formula (VI)

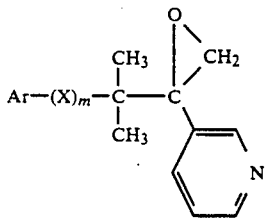

(VI)

in which Ar, X and m have the abovementioned meaning, are reacted with alcohols or thiols of the formula (VII)

$$R^1\text{-ZH} \qquad\qquad (VII)$$

in which $R^1$ and Z have the abovementioned meaning, if appropriate in the presence of a diluent and also if appropriate in the presence of a reaction auxiliary and if appropriate an acid or a metal salt is then adducted.

Finally, it has been found that the new substituted pyridine derivatives of the general formula (I) and also their acid addition salts and metal salt complexes possess a good activity against pests, in particular against fungal pests.

Surprisingly, the substituted pyridine derivatives of the general formula (I) according to the invention show a considerably better fungicidal activity than the substituted pyridine derivatives known from the state of the art, such as, for example, 2-(4-chlorophenoxy)-1-(2,4-dichlorophenyl)-1-(3-pyridyl)-ethanol or 1-(4-chloro-3-methyl-phenoxy)-3,3-dimethyl-2-(3-pyridyl)-2-butanol or 3,3-dimethyl-1-(2-methylphenoxy)-2-(3-pyridyl)-2-butanol or 1-(2,4-dichlorophenoxy)-3,3-dimethyl-2-(3-pyridyl)-2-butanol or their plant-compatible acid addition salts, such as, for example, their naphthalene-1,5-disulphonates, which are closely related compounds chemically and with respect to their action.

Formula (I) provides a general definition of the substituted pyridine derivatives according to the invention. Preferred compounds are those of the formula (I) in which Ar stands for phenyl which is optionally monosubstituted to polysubstituted by identical or different substituents, suitable substituents being: halogen, cyano, nitro, in each case straight-chain or branched alkyl, alkoxy, alkylthio, alkylsulphinylor alkylsulphonyl, each having 1 to 8 carbon atoms, in each case straight-chain or branched halogenoalkyl, halogenoalkoxy, halogenoalkylthio, halogenoalkylsulphinyl or halogenalkylsulphonyl, each having 1 to 4 carbon atoms and 1 to 9 identical or different halogen atoms, in each case straight-chain or branched alkoxycarbonyl or alkoximinoalkyl, each having 1 to 4 carbon atoms in the individual alkyl parts, cycloalkyl having 3 to 6 carbon atoms, divalent dioxyalkylene which is optionally monosubstituted to polysubstituted by identical or different halogen substituents, or phenyl, phenoxy, phenylalkyl or phenylalkoxy which are in each case optionally monosubstituted to polysubstituted in the phenyl part by identical or different halogen substituents and which have if appropriate in each case 1 to 4 carbon atoms in their straight-chain or branched alkyl or alkoxy parts; or for naphthyl which is optionally monosubstituted to polysubstituted by identical or different substituents, suitable substituents being: halogen, cyano or straight-chain or branched alkyl having 1 to 4 carbon atoms;

X stands for oxygen, sulphur, sulphinyl, sulphonyl or for one of the groups $-CH_2-$; $-O-CH_2-$; $-CH_2-O-$; $-O-CH_2-CH_2-$; $-S(O)_n-CH_2-$; $-CH_2-S(O)_n-$ or $-S(O)_n-CH_2-CH_2-$, in which n in each case stands for the number 0,1 or 2, R stands for in each case straight-chain or branched alkyl having 1 to 6 carbon atoms, alkenyl having 3 to 5 carbon atoms or alkinyl having 3 to 5 carbon atoms, for in each case straight-chain or branched alkoxyalkyl or alkylthioalkyl, each having 1 to 6 carbon atoms in the alkoxy or alkylthio part and in each case 1 to 3, in particular 1 carbon atom in the alkyl part, for cycloalkyl having 3 to 7 carbon atoms or for cycloalkylalkyl having 3 to 7 carbon atoms in the cycloalkyl part and 1 to 3 carbon atoms in the straight-chain or branched alkyl part or for phenyl, benzyl, phenylethyl, phenoxymethyl or phenylthiomethyl which are optionally monosubstituted to polysubstituted by identical or different substituents, in which suitable phenyl substitutents in each case are those mentioned for the radical Ar and m stands for the number 0 or 1.

Particularly preferred substituted pyridine derivatives are those of the formula (I) in which Ar stands for phenyl which is optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, ethylthio, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorodichloroethoxy, difluorotrichloroethoxy, pentachloroethoxy, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene, dioxyethylene and also phenyl or phenoxy which are in each case optionally monosubstituted, disubstituted or trisubstituted by fluorine or chlorine; or stands for α-naphthyl or β-naphthyl which are in each case optionally monosubstituted, disubstituted or trisubstituted by identical or different substituents, suitable substituents in each case being: fluorine, chlorine, bromine, cyano, methyl, ethyl, n- or i-propyl;

X stands for oxygen, sulphur, sulphinyl, sulphonyl or for one of the groups $-CH_2-$; $-O-CH_2-$; $-CH_2-O-$; $-O-CH_2-CH_2-$; $-S(O)_n-CH_2-$; $-CH_2-S(O)_n-$ or $-S(O)_n-CH_2-CH_2-$, in which n in each case stands for the number 0, 1 or 2, R stands for methyl, ethyl, n- or i-propyl, n-, i-, s- or t-butyl, allyl, propargyl, for in each case straight-chain or branched alkoxymethyl or alkylthiomethyl, each having 1 to 4 carbon atoms in the alkyl part, for cyclopropyl, cyclopentyl, cyclohexyl, for cyclopropylmethyl, cyclopentylmethyl, cyclohexylmethyl, cyclopropylethyl, cyclopentylethyl or cyclohexylethyl or for phenyl, benzyl, phenylethyl, phenoxymethyl or phenylthiomethyl which are in each case optionally monosubstituted, disubstituted or trisubstituted by identical or different substituents, in which suitable phenyl substituents in each case are those mentioned for the radical Ar, and m stands for the number 0 or 1.

Preferred compounds which can be used according to the invention are also addition products of acids and those substituted pyridine derivatives of the formula (I) in which the substituents Ar, X, m and R have the meaning which has already preferably been mentioned for these substituents.

The acids which can be adducted preferably include hydrohalic acids, such as, for example, hydrochloric acid and hydrobromic acid, in particular hydrochloric acid, and furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as p-toluenesulphonic acid or 1,5-naphthalenedisulphonic acid and also saccharin or thiosaccharin.

In addition, preferred compounds which can be used according to the invention are addition products of salts of metals of main groups II to IV and subgroups I and II and also IV to VIII and those substituted pyridine derivatives of the formula (I) in which the substituents Ar, X, m and R have the meanings which have already preferably been mentioned for these substituents.

Salts of copper, zinc, manganese, magnesium, tin, iron and nickel are particularly preferred here. Possible anions of these salts are those which are derived from those acids which lead to plant-compatible addition products. Particularly preferred acids of this type in this connection are the hydrohalic acids, such as, for example, hydrochloric acid and hydrobromic acid, and furthermore phosphoric acid, nitric acid and sulphuric acid.

The following substituted pyridine derivatives of the general formual (I)

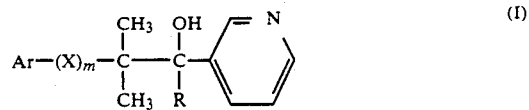

may be mentioned individually in addition to the compounds mentioned in the preparation examples:

| Ar | $-(X)_m-$ | R |
|---|---|---|
| $F_3CO-\text{C}_6\text{H}_4-$ | $-CH_2-$ | $-CH(CH_2)(CH_2)$ (cyclopropyl) |
| $F_3CS-\text{C}_6\text{H}_4-$ | $-CH_2-$ | $-CH(CH_2)(CH_2)$ (cyclopropyl) |
| $F_3CHO-\text{C}_6\text{H}_4-$ | $-CH_2-$ | $-CH_3$ |
| $F_2CHS-\text{C}_6\text{H}_4-$ | $-CH_2-$ | $-CH_3$ |
| $ClF_2CO-\text{C}_6\text{H}_4-$ | $-CH_2-$ | $-CH_3$ |
| $ClF_2CS-\text{C}_6\text{H}_4-$ | $-CH_2-$ | $-CH_3$ |

-continued
| Ar | —(X)$_m$— | R |
|---|---|---|
| 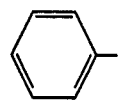 | —CH$_2$— | 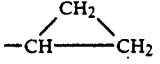 —CH(—CH$_2$)CH$_2$ (cyclopropyl) |
| 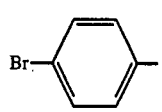 Br-phenyl | —CH$_2$— | —CH(—CH$_2$)CH$_2$ |
| 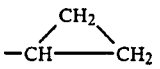 2-Cl, 1-F$_3$CO-phenyl | —CH$_2$— | —CH$_3$ |
| 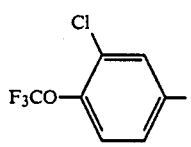 F-phenyl | —CH$_2$— | —CH(—CH$_2$)CH$_2$ |
| 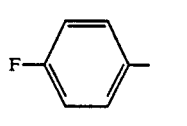 F$_3$C-phenyl | —CH$_2$— | —CH$_3$ |
| 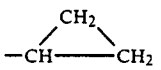 2-Cl, 1-F$_3$C-phenyl | —CH$_2$— | —CH$_3$ |
| 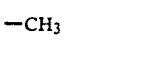 2-Br, 1-F$_3$C-phenyl | —CH$_2$— | —CH$_3$ |
| 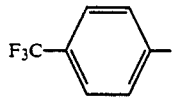 2,3-Cl$_2$-phenyl | —CH$_2$— | —CH(—CH$_2$)CH$_2$ |
| 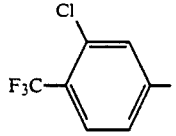 phenyl | —CH$_2$— | —CH(—CH$_2$)CH$_2$ |
| 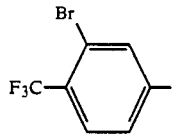 2,4-F$_2$-phenyl | —CH$_2$— | —CH(—CH$_2$)CH$_2$ |
| 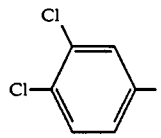 (CF$_3$CHF—O—O—)phenyl | —CH$_2$— | —CH$_3$ |
| 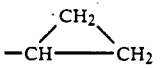 (CF$_2$ dioxole)phenyl | —CH$_2$— | —CH$_3$ |

-continued
| Ar | —(X)$_m$— | R |
|---|---|---|
| 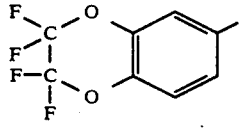 | —CH$_2$— | —CH$_3$ |
| 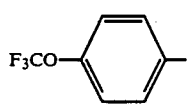 | —CH$_2$— | —CH$_2$—OCH$_3$ |
| 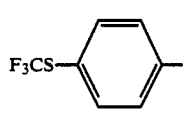 | —CH$_2$— | —CH$_2$—OCH$_3$ |
| 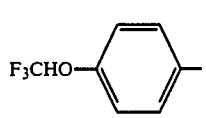 | —CH$_2$— | —CH$_2$—OCH$_3$ |
| 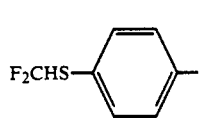 | —CH$_2$— | —CH$_2$—OCH$_3$ |
| 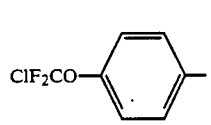 | —CH$_2$— | —CH$_2$—OCH$_3$ |
| 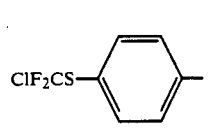 | —CH$_2$— | —CH$_2$—OCH$_3$ |
| 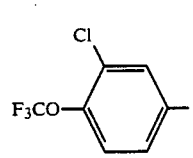 | —CH$_2$— | —CH$_2$—OCH$_3$ |
| 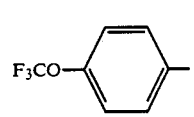 | —CH$_2$— | —CH$_2$—SCH$_3$ |
| 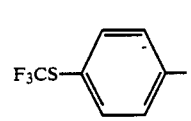 | —CH$_2$— | —CH$_2$—SCH$_3$ |
| 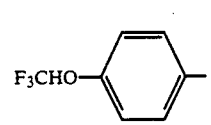 | —CH$_2$— | —CH$_2$—SCH$_3$ |
| 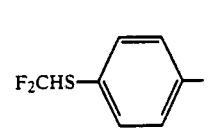 | —CH$_2$— | —CH$_2$—SCH$_3$ |
| 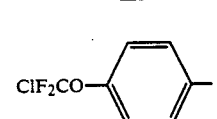 | —CH$_2$— | —CH$_2$—SCH$_3$ |

-continued

| Ar | −(X)$_m$− | R |
|---|---|---|
| 4-ClF$_2$CS−C$_6$H$_4$− | −CH$_2$− | −CH$_2$−SCH$_3$ |
| 2-Cl, 4-(F$_3$CO)−C$_6$H$_3$− | −CH$_2$− | −CH$_2$−SCH$_3$ |
| C$_6$H$_5$− | — | −CH$_3$ |
| 4-F$_3$CO−C$_6$H$_4$− | — | −CH$_3$ |
| 4-Br−C$_6$H$_4$− | — | −CH$_3$ |
| 4-F$_3$CS−C$_6$H$_4$− | — | −CH$_3$ |
| 2-Cl, 4-(F$_3$CO)−C$_6$H$_3$− | — | −CH$_3$ |
| 4-F$_3$CHO−C$_6$H$_4$− | — | −CH$_3$ |
| 4-F−C$_6$H$_4$− | — | −CH$_3$ |
| 2,3-F$_2$−C$_6$H$_3$− | — | −CH$_3$ |
| 2-Br, 3-(F$_3$CS)−C$_6$H$_3$− | — | −CH$_3$ |
| 2,4-Cl$_2$−C$_6$H$_3$− | — | −CH$_3$ |

-continued

| Ar | —(X)$_m$— | R |
|---|---|---|
| 3,4-dichlorophenyl | — | —CH$_3$ |
| 2-bromophenyl | — | —CH$_3$ |
| 2-chlorophenyl | — | —CH$_3$ |
| 2-fluorophenyl | — | —CH$_3$ |
| 4-(trifluoromethyl)phenyl | — | —CH$_3$ |
| 3-fluoro-4-(trifluoromethyl)phenyl | — | —CH$_3$ |
| 4-(chlorodifluoromethoxy)phenyl | — | —CH$_3$ |
| 4-chlorophenyl | —O—CH$_2$—CH$_2$— | —CH$_2$—OCH$_3$ |
| 4-bromophenyl | —O—CH$_2$—CH$_2$— | —CH$_2$—OCH$_3$ |
| 3,4-dichlorophenyl | —O—CH$_2$—CH$_2$— | —CH$_2$—OCH$_3$ |
| 2,4-difluorophenyl | —O—CH$_2$—CH$_2$— | —CH$_2$—OCH$_3$ |
| 4-(trifluoromethoxy)phenyl | —O—CH$_2$—CH$_2$— | —CH$_2$—OCH$_3$ |

-continued

| Ar | —(X)$_m$— | R |
|---|---|---|
| F$_3$CS—⌬— | —O—CH$_2$—CH$_2$— | —CH$_2$—OCH$_3$ |
| 2-Cl, 4-(F$_3$CO)—⌬— | —O—CH$_2$—CH$_2$— | —CH$_2$—OCH$_3$ |
| F$_2$CHO—⌬— | —O—CH$_2$—CH$_2$— | —CH$_2$—OCH$_3$ |
| ClF$_2$CO—⌬— | —O—CH$_2$—CH$_2$— | —CH$_2$—OCH$_3$ |
| Cl—⌬— | —O—CH$_2$—CH$_2$— | —CH$_2$—SCH$_3$ |
| Br—⌬— | —O—CH$_2$—CH$_2$— | —CH$_2$—SCH$_3$ |
| 2,4-Cl$_2$—⌬— | —O—CH$_2$—CH$_2$— | —CH$_2$—SCH$_3$ |
| 2,4-F$_2$—⌬— | —O—CH$_2$—CH$_2$— | —CH$_2$—SCH$_3$ |
| F$_3$CO—⌬— | —O—CH$_2$—CH$_2$— | —CH$_2$—SCH$_3$ |
| F$_3$CS—⌬— | —O—CH$_2$—CH$_2$— | —CH$_2$—SCH$_3$ |
| 2-Cl, 4-(F$_3$CO)—⌬— | —O—CH$_2$—CH$_2$— | —CH$_2$—SCH$_3$ |
| F$_2$CHO—⌬— | —O—CH$_2$—CH$_2$— | —CH$_2$—SCH$_3$ |

-continued

| Ar | —(X)$_m$— | R |
|---|---|---|
| 4-ClF$_2$CO-C$_6$H$_4$- | —O—CH$_2$—CH$_2$— | —CH$_2$—SCH$_3$ |
| 4-Cl-C$_6$H$_4$- | —O—CH$_2$—CH$_2$— | —CH$_2$—O—C$_6$H$_4$-4-Cl |
| 4-Br-C$_6$H$_4$- | —O—CH$_2$—CH$_2$— | —CH—O—C$_6$H$_4$-4-Cl |
| 2,4-Cl$_2$-C$_6$H$_3$- | —O—CH$_2$—CH$_2$— | —CH$_2$—O—C$_6$H$_4$-4-Cl |
| 2,4-F$_2$-C$_6$H$_3$- | —O—CH$_2$—CH$_2$— | —CH$_2$—O—C$_6$H$_4$-4-Cl |
| 4-F$_3$CO-C$_6$H$_4$- | —O—CH$_2$—CH$_2$— | —CH$_2$—O—C$_6$H$_4$-4-Cl |
| 4-F$_3$CS-C$_6$H$_4$- | —O—CH$_2$—CH$_2$— | —CH$_2$—O—C$_6$H$_4$-4-Cl |
| 2-Cl-4-F$_3$CO-C$_6$H$_3$- | —O—CH$_2$—CH$_2$— | —CH$_2$—O—C$_6$H$_4$-4-Cl |
| 4-F$_2$CHO-C$_6$H$_4$- | —O—CH$_2$—CH$_2$— | —CH$_2$—O—C$_6$H$_4$-4-Cl |
| 4-ClF$_2$CO-C$_6$H$_4$- | —O—CH$_2$—CH$_2$— | —CH$_2$—O—C$_6$H$_4$-4-Cl |
| 4-F$_3$CO-C$_6$H$_4$- | —O—CH$_2$— | —CH$_3$ |
| 4-F$_3$CS-C$_6$H$_4$- | —O—CH$_3$— | —CH$_3$ |
| 4-F$_2$CHO-C$_6$H$_4$- | —O—CH$_2$— | —CH$_3$ |

-continued

| Ar | —(X)ₘ— | R |
|---|---|---|
| F₂CHS—⌬— | —O—CH₂— | —CH₃ |
| ClF₂CO—⌬— | —O—CH₂— | —CH₃ |
| ClF₂CS—⌬— | —O—CH₂— | —CH₃ |
| F₃CO—⌬(Cl)— | —O—CH₂— | —CH₃ |
| F₃CO—⌬— | —CH₂— | —CH₂—CH=CH₂ |
| F₃CS—⌬— | —CH₂— | —CH₂—CH=CH₂ |
| F₂CHO—⌬— | —CH₂— | —CH₂—CH=CH₂ |
| ClF₂CO—⌬— | —CH₂— | —CH₂—CH=CH₂ |
| F₂CHS—⌬— | —CH₂— | —CH₂—CH=CH₂ |
| ClF₂CS—⌬— | —CH₂— | —CH₂—CH=CH₂ |
| Cl—⌬— | —CH₂— | —CH₂—CH=CH₂ |
| Br—⌬— | —CH₂— | —CH₂—CH=CH₂ |
| F₃CO—⌬(Cl)— | —CH₂— | —CH₂—CH=CH₂ |

-continued
| Ar | —(X)$_m$— | R |
|---|---|---|
| 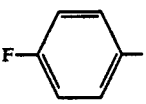 | —CH$_2$— | —CH$_2$—CH=CH$_2$ |
| 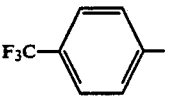 | —CH$_2$— | —CH$_2$—CH=CH$_2$ |
| 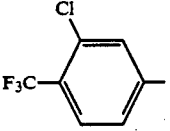 | —CH$_2$— | —CH$_2$—CH=CH$_2$ |
| 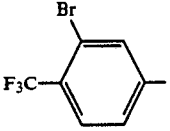 | —CH$_2$— | —CH$_2$—CH=CH$_2$ |
| 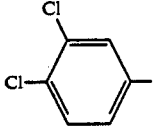 | —CH$_2$— | —CH$_2$—CH=CH$_2$ |
| 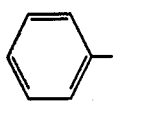 | —CH$_2$— | —CH$_2$—CH=CH$_2$ |
| 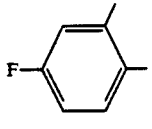 | —CH$_2$— | —CH$_2$—CH=CH$_2$ |
| 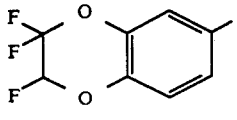 | —CH$_2$— | —CH$_2$—CH=CH$_2$ |
| 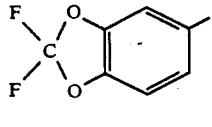 | —CH$_2$— | —CH$_2$—CH=CH$_2$ |
| 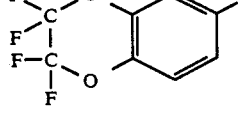 | —CH$_2$— | —CH$_2$—CH=CH$_2$ |
| 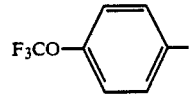 | —CH$_2$— | —CH$_2$—C≡CH |
| 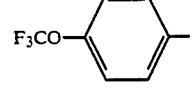 | —CH$_2$— | —CH$_2$—C≡CH |

-continued

| Ar | —(X)$_m$— | R |
|---|---|---|
| F$_2$CHO—〔Ph〕— | —CH$_2$— | —CH$_2$—C≡CH |
| F$_2$CHS—〔Ph〕— | —CH$_2$— | —CH$_2$—C≡CH |
| ClF$_2$CO—〔Ph〕— | —CH$_2$— | —CH$_2$—C≡CH |
| ClF$_2$CS—〔Ph〕— | —CH$_2$— | —CH$_2$—C≡CH |
| Cl—〔Ph〕— | —CH$_2$— | —CH$_2$—C≡CH |
| Br—〔Ph〕— | —CH$_2$— | —CH$_2$—C≡CH |
| F$_3$CO—〔Ph(2-Cl)〕— | —CH$_2$— | —CH$_2$—C≡CH |
| F—〔Ph〕— | —CH$_2$— | —CH$_2$—C≡CH |
| F$_3$C—〔Ph〕— | —CH$_2$— | —CH$_2$—C≡CH |
| F$_3$C—〔Ph(2-Cl)〕— | —CH$_2$— | —CH$_2$—C≡CH |
| F$_3$C—〔Ph(2-Br)〕— | —CH$_3$— | —CH$_2$—C≡CH |
| Cl,Cl—〔Ph〕— | —CH$_2$— | —CH$_2$—C≡CH |

-continued
| Ar | —(X)$_m$— | R |
|---|---|---|
| 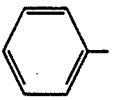 | —CH$_2$— | —CH$_2$—C≡CH |
| 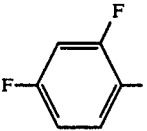 | —CH$_2$— | —CH$_2$—C≡CH |
| 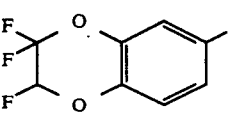 | —CH$_2$— | —CH$_2$—C≡CH |
| 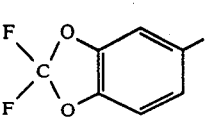 | —CH$_2$— | —CH$_2$—C≡CH |
| 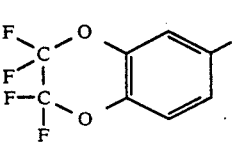 | —CH$_2$— | —CH$_2$—C≡CH |
| 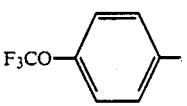 | O | 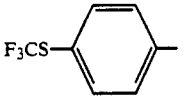 |
| 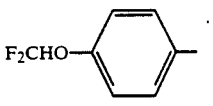 | O | 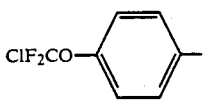 |
| 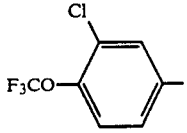 | O | 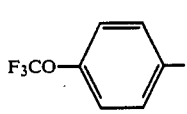 |
| 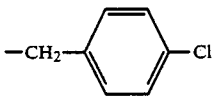 | O | 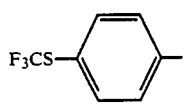 |
| 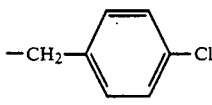 | O | 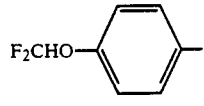 |
| 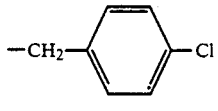 | —CH$_2$— | —CH$_2$—⟨C$_6$H$_4$⟩—Cl |
| F$_3$CS—⟨C$_6$H$_4$⟩— | —CH$_2$— | —CH$_2$—⟨C$_6$H$_4$⟩—Cl |
| F$_2$CHO—⟨C$_6$H$_4$⟩— | —CH$_2$— | —CH$_2$—⟨C$_6$H$_4$⟩—Cl |

-continued

| Ar | —(X)$_m$— | R |
|---|---|---|
| 4-(F$_2$CHS)-C$_6$H$_4$— | —CH$_2$— | —CH$_2$-(4-Cl-C$_6$H$_4$) |
| 4-(ClF$_2$CO)-C$_6$H$_4$— | —CH$_2$— | —CH$_2$-(4-Cl-C$_6$H$_4$) |
| 4-(ClF$_2$CS)-C$_6$H$_4$— | —CH$_2$— | —CH$_2$-(4-Cl-C$_6$H$_4$) |
| 4-Cl-C$_6$H$_4$— | —CH$_2$— | —CH$_2$-(4-Cl-C$_6$H$_4$) |
| 4-Br-C$_6$H$_4$— | —CH$_2$— | —CH$_2$-(4-Cl-C$_6$H$_4$) |
| 3-Cl-4-(F$_3$CO)-C$_6$H$_3$— | —CH$_2$— | —CH$_2$-(4-Cl-C$_6$H$_4$) |
| 4-F-C$_6$H$_4$— | —CH$_2$— | —CH$_2$-(4-Cl-C$_6$H$_4$) |
| 4-(F$_3$C)-C$_6$H$_4$— | —CH$_2$— | —CH$_2$-(4-Cl-C$_6$H$_4$) |
| 3-Cl-4-(F$_3$C)-C$_6$H$_3$— | —CH$_2$— | —CH$_2$-(4-Cl-C$_6$H$_4$) |
| 3-Br-4-(F$_3$C)-C$_6$H$_3$— | —CH$_2$— | —CH$_2$-(4-Cl-C$_6$H$_4$) |
| 3,4-Cl$_2$-C$_6$H$_3$— | —CH$_2$— | —CH$_2$-(4-Cl-C$_6$H$_4$) |
| C$_6$H$_5$— | —CH$_2$— | —CH$_2$-(4-Cl-C$_6$H$_4$) |

-continued

| Ar | —(X)$_m$— | R |
|---|---|---|
| 2,4-difluorophenyl | —CH$_2$— | —CH$_2$-C$_6$H$_4$-Cl |
| 2,2,3-trifluoro-1,4-benzodioxin-6-yl | —CH$_2$— | —CH$_2$-C$_6$H$_4$-Cl |
| 2,2-difluoro-1,3-benzodioxol-5-yl | —CH$_2$— | —CH$_2$-C$_6$H$_4$-Cl |
| 2,2,3,3-tetrafluoro-1,4-benzodioxin-6-yl | —CH$_2$— | —CH$_2$-C$_6$H$_4$-Cl |
| 4-(trifluoromethoxy)phenyl | O | —CH$_2$—CH=CH$_2$ |
| 4-(trifluoromethylthio)phenyl | O | —CH$_2$—CH=CH$_2$ |
| 4-(difluoromethoxy)phenyl | O | —CH$_2$—CH=CH$_2$ |
| 4-(chlorodifluoromethoxy)phenyl | O | —CH$_2$—CH=CH$_2$ |
| 2-chloro-4-(trifluoromethoxy)phenyl | O | —CH$_2$—CH=CH$_2$ |
| 2,4-difluorophenyl | O | —CH$_2$—CH=CH$_2$ |
| 2,4-dichlorophenyl | O | —CH$_2$—CH=CH$_2$ |
| 4-chlorophenyl | O | —CH$_2$—CH=CH$_2$ |

-continued

| Ar | −(X)$_m$− | R |
|---|---|---|
| Br-C$_6$H$_4$- | O | −CH$_2$−CH=CH$_2$ |
| NC-C$_6$H$_4$- | O | −CH$_2$−CH=CH$_2$ |
| 2,4-F$_2$-C$_6$H$_3$- | O | −CH(−CH$_2$−CH$_2$) (cyclopropyl) |
| 2,4-Cl$_2$-C$_6$H$_3$- | O | −CH(−CH$_2$−CH$_2$) (cyclopropyl) |
| 4-Cl-C$_6$H$_4$- | O | −CH(−CH$_2$−CH$_2$) (cyclopropyl) |
| 4-Br-C$_6$H$_4$- | O | −CH(−CH$_2$−CH$_2$) (cyclopropyl) |
| 4-NC-C$_6$H$_4$- | O | −CH(−CH$_2$−CH$_2$) (cyclopropyl) |
| C$_6$H$_5$- | O | −CH(−CH$_2$−CH$_2$) (cyclopropyl) |
| C$_6$H$_5$- | O | −CH$_2$−CH=CH$_2$ |
| 4-F$_3$CO-C$_6$H$_4$- | O | −CH$_2$−C≡CH |
| 4-F$_3$CS-C$_6$H$_4$- | O | −CH$_2$−C≡CH |
| 4-F$_2$CHO-C$_6$H$_4$- | O | −CH$_2$−C≡CH |
| C$_6$H$_5$- | O | −CH$_2$−C≡CH |

-continued

| Ar | —(X)$_m$— | R |
|---|---|---|
| ClF$_2$CO—⟨C$_6$H$_4$⟩— | O | —CH$_2$—C≡CH |
| ClF$_2$CS—⟨C$_6$H$_4$⟩— | O | —CH$_2$—C≡CH |
| 2-Cl, 4-(F$_3$CO)—⟨C$_6$H$_3$⟩— | O | —CH$_2$—C≡CH |
| 2,4-F$_2$—⟨C$_6$H$_3$⟩— | O | —CH$_2$—C≡CH |
| 2,4-Cl$_2$—⟨C$_6$H$_3$⟩— | O | —CH$_2$—C≡CH |
| 4-Cl—⟨C$_6$H$_4$⟩— | O | —CH$_2$—C≡CH |
| 4-Br—⟨C$_6$H$_4$⟩— | O | —CH$_2$—C≡CH |
| 4-NC—⟨C$_6$H$_4$⟩— | O | —CH$_2$—C≡CH |
| 4-F$_3$CO—⟨C$_6$H$_4$⟩— | O | —CH$_2$—⟨C$_6$H$_4$⟩—Cl |
| 4-F$_3$CS—⟨C$_6$H$_4$⟩— | O | —CH$_2$—⟨C$_6$H$_4$⟩—Cl |
| 4-F$_2$CHO—⟨C$_6$H$_4$⟩— | O | —CH$_2$—⟨C$_6$H$_4$⟩—Cl |
| ⟨C$_6$H$_5$⟩— | O | —CH$_2$—⟨C$_6$H$_4$⟩—Cl |

-continued

| Ar | —(X)$_m$— | R |
|---|---|---|
| ClF$_2$CO—C$_6$H$_4$— | O | —CH$_2$—C$_6$H$_4$—Cl |
| ClF$_2$CS—C$_6$H$_4$— | O | —CH$_2$—C$_6$H$_4$—Cl |
| F$_3$CO—C$_6$H$_3$(Cl)— | O | —CH$_2$—C$_6$H$_4$—Cl |
| F,F—C$_6$H$_3$— (2,4-difluoro) | O | —CH$_2$—C$_6$H$_4$—Cl |
| Cl,Cl—C$_6$H$_3$— (2,4-dichloro) | O | —CH$_2$—C$_6$H$_4$—Cl |
| Cl—C$_6$H$_4$— | O | —CH$_2$—C$_6$H$_4$—Cl |
| Br—C$_6$H$_4$— | O | —CH$_2$—C$_6$H$_4$—Cl |
| NC—C$_6$H$_4$— | O | —CH$_2$—C$_6$H$_4$—Cl |
| F$_3$CO—C$_6$H$_4$— | O | —CH$_2$—O—C$_6$H$_4$—Cl |
| F$_3$CS—C$_6$H$_4$— | O | —CH$_2$—O—C$_6$H$_4$—Cl |
| F$_2$CHO—C$_6$H$_4$— | O | —CH$_2$—O—C$_6$H$_4$—Cl |
| C$_6$H$_5$— | O | —CH$_2$—O—C$_6$H$_4$—Cl |
| ClF$_2$CO—C$_6$H$_4$— | O | —CH$_2$—O—C$_6$H$_4$—Cl |

-continued

| Ar | —(X)$_m$— | R |
|---|---|---|
| 4-(ClF$_2$CS)-C$_6$H$_4$— | 0 | —CH$_2$—O—C$_6$H$_4$-4-Cl |
| 2-Cl-4-(F$_3$CO)-C$_6$H$_3$— | 0 | —CH$_2$—O—C$_6$H$_4$-4-Cl |
| 2,4-F$_2$-C$_6$H$_3$— | 0 | —CH$_2$—O—C$_6$H$_4$-4-Cl |
| 2,4-Cl$_2$-C$_6$H$_3$— | 0 | —CH$_2$—O—C$_6$H$_4$-4-Cl |
| 4-Cl-C$_6$H$_4$— | 0 | —CH$_2$—O—C$_6$H$_4$-4-Cl |
| 4-Br-C$_6$H$_4$— | 0 | —CH$_2$—O—C$_6$H$_4$-4-Cl |
| 4-NC-C$_6$H$_4$— | 0 | —CH$_2$—O—C$_6$H$_4$-4-Cl |
| 4-(F$_3$CO)-C$_6$H$_4$— | 0 | —CH$_2$—S—C$_6$H$_4$-4-Cl |
| 4-(F$_3$CS)-C$_6$H$_4$— | 0 | —CH$_2$—S—C$_6$H$_4$-4-Cl |
| 4-(F$_2$CHO)-C$_6$H$_4$— | 0 | —CH$_2$—S—C$_6$H$_4$-4-Cl |
| C$_6$H$_5$— | 0 | —CH$_2$—S—C$_6$H$_4$-4-Cl |
| 4-(ClF$_2$CO)-C$_6$H$_4$— | 0 | —CH$_2$—S—C$_6$H$_4$-4-Cl |

-continued

| Ar | −(X)$_m$− | R |
|---|---|---|
| ClF$_2$CS-C$_6$H$_4$- | O | -CH$_2$-S-C$_6$H$_4$-Cl |
| F$_3$CO-(2-Cl)C$_6$H$_3$- | O | -CH$_2$-S-C$_6$H$_4$-Cl |
| 2,4-F$_2$C$_6$H$_3$- | O | -CH$_2$-S-C$_6$H$_4$-Cl |
| 2,4-Cl$_2$C$_6$H$_3$- | O | -CH$_2$-S-C$_6$H$_4$-Cl |
| 4-ClC$_6$H$_4$- | O | -CH$_2$-S-C$_6$H$_4$-Cl |
| 4-BrC$_6$H$_4$- | O | -CH$_2$-S-C$_6$H$_4$-Cl |
| 4-NCC$_6$H$_4$- | O | -CH$_2$-S-C$_6$H$_4$-Cl |
| F$_3$CO-C$_6$H$_4$- | O | -CH$_2$-OCH$_3$ |
| F$_3$CS-C$_6$H$_4$- | O | -CH$_2$-OCH$_3$ |
| F$_2$CHO-C$_6$H$_4$- | O | -CH$_2$-OCH$_3$ |
| C$_6$H$_5$- | O | -CH$_2$-OCH$_3$ |
| ClF$_2$CO-C$_6$H$_4$- | O | -CH$_2$-OCH$_3$ |
| ClF$_2$CS-C$_6$H$_4$- | O | -CH$_2$-OCH$_3$ |

-continued

| Ar | —(X)$_m$— | R |
|---|---|---|
| 2-Cl, 4-(F$_3$CO)-phenyl | 0 | —CH$_2$—OCH$_3$ |
| 2,4-difluorophenyl | 0 | —CH$_2$—OCH$_3$ |
| 2,4-dichlorophenyl | 0 | —CH$_2$—OCH$_3$ |
| 4-Cl-phenyl | 0 | —CH$_2$—OCH$_3$ |
| 4-Br-phenyl | 0 | —CH$_2$—OCH$_3$ |
| 4-NC-phenyl | 0 | —CH$_2$—OCH$_3$ |
| 4-(F$_3$CO)-phenyl | 0 | —CH$_2$—SCH$_3$ |
| 4-(F$_3$CS)-phenyl | 0 | —CH$_2$—SCH$_3$ |
| 4-(F$_2$CHO)-phenyl | 0 | —CH$_2$—SCH$_3$ |
| phenyl | 0 | —CH$_2$—SCH$_3$ |
| 4-(ClF$_2$CO)-phenyl | 0 | —CH$_2$—SCH$_3$ |
| 4-(ClF$_2$CS)-phenyl | 0 | —CH$_2$—SCH$_3$ |

-continued

| Ar | $-(X)_m-$ | R |
|---|---|---|
| 2-Cl, 4-(F₃CO)-phenyl | O | $-CH_2-SCH_3$ |
| 2,4-difluorophenyl | O | $-CH_2-SCH_3$ |
| 2,4-dichlorophenyl | O | $-CH_2-SCH_3$ |
| 4-chlorophenyl | O | $-CH_2-SCH_3$ |
| 4-bromophenyl | O | $-CH_2-SCH_3$ |
| 4-cyanophenyl | O | $-CH_2-SCH_3$ |

If, for example, 3-(4-chlorophenoxy)-3-methyl-butan-2-one and 3-pyridylmagnesium bromide are used as starting materials, then the course of the reaction of process (a) according to the invention can be represented by the following equation:

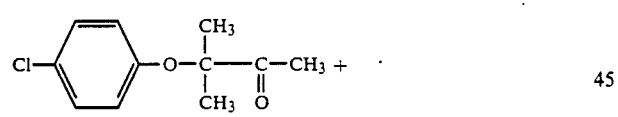

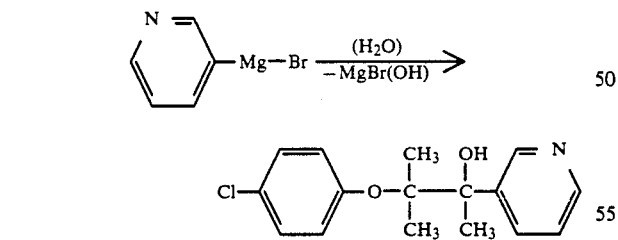

If, for example, 3-(4-fluorophenyl)-2,2-dimethyl-1-(3-pyridyl)-propan-1-one and allylmagnesium bromide are used as starting materials, then the course of the reaction of process (b) according to the invention can be represented by the following equation:

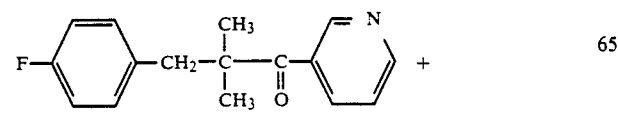

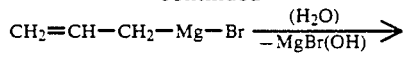

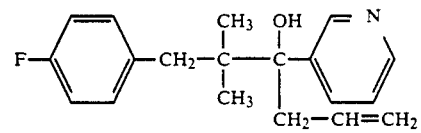

If, for example, 2-[2-(2,4-dichlorophenoxy)-2-propyl]-2-(3-pyridyl)-oxirane and 4-chlorophenol are used as starting materials, then the course of the reaction of process (c) according to the invention can be represented by the following equation:

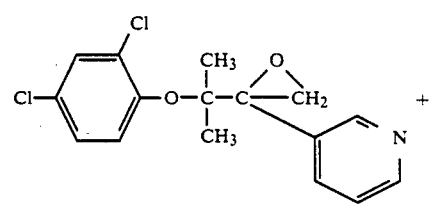

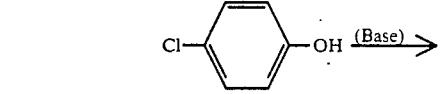

-continued

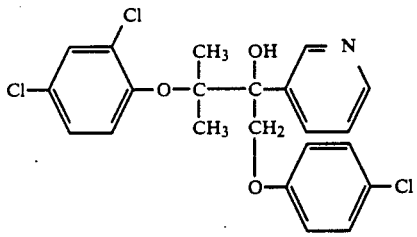

Formula (II) provides a general definition of the ketones required as starting materials for carrying out process (a) according to the invention. In this formula (II), R, Ar, X and m preferably stand for those radicals and indices which have already been mentioned as preferred for these substituents and indices in connection with the description of the substances of the formula (I) according to the invention.

The ketones of the formula (II) are known or can be obtained in analogy to known processes (compare, for example, DE-OS (German Published Specification) 3,210,725 or DE-OS (German Published Specification) 3,048,266).

Formula (III) provides a general definition of the pyridyl Grignard compounds furthermore required as starting materials for carrying out process (a) according to the invention. In this formula (III), $Hal^1$ preferably stands for chlorine, bromine or iodine.

The pyridyl Grignard compounds of the formula (III) are also known (compare, for example, EP 221,844 or Angew. Chem. Int. Ed. Engl. 8, 279 [1969]).

Formula (IV) provides a general definition of the pyridyl ketones required as starting materials for carrying out process (b) according to the invention. In this formula (IV), Ar, X and m preferably stand for those radicals and indices which have already been mentioned as preferred for these substituents and indices in connection with the description of the substances of the formula (I) according to the invention.

Some of the pyridyl ketones of the formula (IV) are known (compare, for example, EP 221,844) or are compounds of a previously unpublished commonly assigned application and are obtainable in analogy to known processes, for example when esters of the formula (VIII)

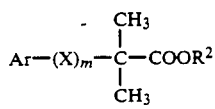

in which $R^2$ stands for alkyl, in particular for methyl or ethyl, are reacted with pyridyl Grignard compounds of the formula (III)

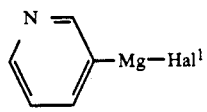

in which $Hal^1$ stands for halogen, in particular for chlorine, bromine or iodine, if appropriate in the presence of a diluent, such as, for example, diethyl ether or tetrahydrofuran, at temperatures between $-20°$ C. and $+60°$ C.; or when carbinols of the formula (IX)

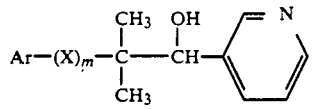

in which Ar, X and m have the abovementioned meaning, are oxidized with a customary oxidant such as, for example, chromium trioxide in acetic acid (compare for example, Tetrahedron Letters 1978, 1651-1660).

The esters of the formula (VIII) are known or are obtainable in analogy to known processes (compare, for example, EP 221,844 or Przem. Chem. 59, 495-498 [1980] or CA 94: 102,975e).

Some of the carbinols of the formula (IX) are known (compare EP 221,844), and some are the subject of a previously unpublished commonly assigned patent application and are obtainable in analogy to known processes.

Formula (V) provides a general definition of the alkyl Grignard compounds furthermore required as starting materials for carrying out process (b) according to the invention. In this formula (V), R preferably stands for those radicals which have already been mentioned as preferred for these substituents in connection with the description of the substances of the formula (I) according to the invention.

$Hal^2$ preferably stands for chlorine, bromine or iodine.

The alkyl Grignard compounds of the formula (V) are generally known compounds of organic chemistry.

Formula (VI) provides a general definition of the pyridyl oxiranes required as starting materials for carrying out process (c) according to the invention. In this formula (VI), Ar, X and m preferably stand for those radicals and indices which have already been mentioned as preferred for these substituents and indices in connection with the description of the substances of the formula (I) according to the invention.

The pyridyl oxiranes of the formula (VI) are hitherto unknown.

They are obtained when pyridyl ketones of the formula (IV)

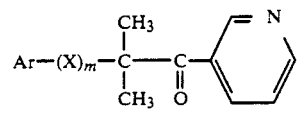

in which Ar, X and m have the abovementioned meaning, are either reacted with dimethyloxosulphonium methylide of the formula (X)

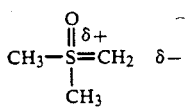

in a known manner in the presence of a diluent such as, for example, dimethyl sulphoxide, at temperatures between 20° C. and 80° C. (compare, for example, J. Amer. Chem. Soc. 87, 1363-1364 [1965]), or with trimethylsulphonium methylsulphat of the formula (XI)

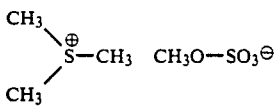

(XI)

in a known manner in the presence of a diluent such as, for example, acetonitrile and in the presence of a base, such as, for example, sodium methylate, at temperatures between 0° C. and 60° C. (compare, for example, Heterocycles 8, 397 [1977]).

The pyridyl oxiranes of the formula (VI) which are thus obtainable can be further reacted directly from the reaction mixture without isolation, if desired.

Formula (VII) provides a general definition of the alcohols or thiols furthermore required as starting materials for carrying out process (c) according to the invention. In this formula (VII), $R^1$ preferably stands for straight-chain or branched alkyl having 1 to 6 carbon atoms or for phenyl which is optionally monosubstituted to polysubstituted by identical or different substituents, suitable substituents being: halogen, cyano, nitro, in each case straight-chain or branched alkyl, alkoxy, alkylthio, alkylsulphinyl or alkylsulphonyl, each having 1 to 8 carbon atoms, in each case straight-chain or branched halogenoalkyl, halogenoalkoxy, halogenoalkylthio, halogenoalkylsulphinyl or halogenoalkylsulphonyl, each having 1 to 4 carbon atoms and 1 to 9 identical or different halogen atoms, in each case straight-chain or branched alkoxycarbonyl or alkoximinoalkyl, each having 1 to 4 carbon atoms in the individual alkyl parts, cycloalkyl having 3 to 6 carbon atoms, divalent dioxyalkylene which is optionally monosubstituted to polysubstituted by identical or different halogen substituents, or phenyl, phenoxy, phenylalkyl or phenylalkoxy which are in each case optionally monosubstituted to polysubstituted in the phenyl part by identical or different halogen substituents and which have if appropriate in each case 1 to 4 carbon atoms in their straight-chain or branched alkyl or alkoxy parts, $R^1$ particularly preferably stands for methyl, ethyl, n- or i-propyl, n-, i, s- or t-butyl or for phenyl which is optionally monosubstituted to trisubstituted by identical or different substituents, suitable substituents being; fluorine, chlorine, bromine, cyano, nitro, methyl, ethyl, n- or i-propyl, n-, i, s- or t-butyl, methoxy, ethoxy, n- or i-propoxy, methylthio, ethylthio, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorodichloroethoxy, difluorotrichlorethoxy, pentachloroethoxy, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene or dioxyethylene, and also phenyl or phenoxy which are in each case optionally monosubstituted, disubstituted or trisubstituted by fluorine or chlorine.

Z preferably stands for oxygen or sulphur.

The alcohols or thiols of the formula (VII) are generally known compounds of organic chemistry.

Suitable diluents for carrying out process (a) according to the invention are inert organic solvents. In particular, these include aliphatic, alicyclic or aromatic hydrocarbons, such as, for example, benzine, benzene, toluene, xylene, petroleum ether, hexane or cyclohexane, ethers, such as diethyl ether, diisopropyl ether, dioxane, tetrahydrofuran or ethylene glycol dimethyl ether or ethylene glycol diethyl ether or amides, such as hexamethylphosphoric triamide.

The reaction temperatures can be varied within a substantial range when carrying out process (a) according to the invention. In general, the reaction is carried out at temperatures between −50° C. and +150° C., preferably at temperatures between −20° C. and +120° C.

For carrying out process (a) according to the invention, 1.0 to 3.0 moles, preferably 1.0 to 1.5 moles, of pyridyl Grignard compound of the formula (III) are generally employed per mole of ketone of the formula (II). The reaction is carried out according to customary methods.

If necessary, the reaction can be carried out in the presence of a suitable inert gas, such as, for example, nitrogen or helium. It is also possible to produce the pyridyl Grignard compound of the formula (III) employed as the reaction component from suitable starting compounds, such as, for example, 3-bromopyridine and isopropylmagnesium bromide in the reaction vessel directly in a previous reaction and to further react it without isolation in the one-pot process with the ketones of the formula (II).

The reaction products are worked up and isolated by customary methods (compare the preparation examples).

Suitable diluents for carrying out process (b) according to the invention are also inert organic solvents. The organic solvents mentioned as diluents in process (a) are preferably used.

The reaction temperatures can be varied within a substantial range when carrying out process (b) according to the invention. In general, the reaction is carried out at temperatures between −50° C. and +150° C., preferably at temperatures between −20° C. and +120° C.

For carrying out process (b) according to the invention, 1.0 to 3.0 moles, preferably 1.0 to 1.5 moles, of alkyl Grignard compound of the formula (V) are generally employed per mole of pyridylketone of the formula (IV). The reaction is carried out, and the reaction products are worked up and isolated by generally customary methods.

Suitable diluents for carrying out process (c) according to the invention are inert organic solvents. In particular, these include aliphatic, alicyclic or aromatic hydrocarbons, such as, for example, benzine, benzene, toluene, xylene, petroleum ether, hexane or cyclohexane, ethers, such as diethyl ether, dioxane, tetrahydrofuran or ethylene glycol dimethyl ether or ethylene glcyol diethyl ether, ketones, such as acetone or butanone, nitriles, such as acetonitrile or propionitrile or amides, such as dimethylformamide, dimethylacetamide, N-methylformanilide, N-methylpyrrolidone or hexamethylphosphoric triamide.

If desired, it is also possible to employ the alcohols or thiols of the formula (VII) used as reaction components simultaneously as diluent in a corresponding excess.

Process (c) according to the invention is preferably carried out in the presence of a suitable basic reaction auxiliary. Those which are suitable are all conventionally utilizable inorganic and organic bases. Hydrides, hydroxides, amides, carbonates or hydrogen carbonates of alkali metals, such as, for example, sodium hydride, sodium amide, sodium hydroxide, sodium carbonate or sodium hydrogen carbonate and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

The reaction temperatures can be varied within a substantial range when carrying out process (c) according to the invention. In general, the reaction is carried out at temperatures between 0° C. and 200° C., preferably at temperatures between 60° C. and 150° C.

For carrying out process (c) according to the invention, 1.0 to 20.0 moles, preferably 1.0 to 5.0 moles, of alcohol or thiol of the formula (VII) and if appropriate 1.0 to 5.0 moles, preferably 1.0 to 2.0 moles, of basic reaction auxiliary are generally employed per mole of pyridyloxirane of the formula (VI).

The reaction is carried out, and the reaction products are worked up and isolated by generally customary methods (compare, for example, DE-OS (German Published Specification) 3,427,844).

If desired, the substituted pyridine derivatives of the formula (I) obtainable with the aid of processes (a), (b) or (c) according to the invention can be derivatized by customary methods, for example by reacting the hydroxyl group with customary alkylation or acylation agents. The alkylation or acylation products of the compounds of the formula (I) according to the invention thus obtained also possess good fungicidal activity.

For the preparation of plant-compatible acid addition salts of the compounds of the formula (I), suitable acids are preferably the following: hydrohalic acids, such as, for example, hydrochloric acid and hydrobromic acid, in particular hydrochloric acid, and furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as, for example, p-toluenesulphonic acid and 1,5-naphthalenedisulphonic acid and also saccharin or thiosaccharin.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and can be isolated in a known manner, for example by filtering off, and can be purified if desired by washing with an inert organic solvent.

For the preparation of metal salt complexes of the compounds of the formula (I), suitable salts are preferably those of metals of main groups II to IV and subgroups I and II and also IV to VIII, where copper, zinc, manganese, magnesium, tin, iron and nickel may be mentioned, for example.

Possible anions of salts are those which are preferably derived from the following acids: hydrohalic acids, such as, for example, hydrochloric acid and hydrobromic acid, and furthermore phosphoric acid, nitric acid and sulphuric acid.

The metal salt complexes of compounds of the formula (I) can be obtained in a simple manner by customary processes, thus, for example, by dissolving the metal salt in alcohol, for example ethanol and adding it to the compound of the formula (I). Metal salt complexes can be isolated in a known manner, for example by filtering off and can be purified by recrystallization, if desired.

The active compounds according to the invention exhibit a strong action against pests and can be practically employed for combating undesired harmful organisms. The active compounds can be employed for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some pathogens of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fursarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example. *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seed, and of the soil.

The active compounds according to the invention can be used with particularly good effect for combating cereal diseases, such as, for example, against the pathogen of powdery mildew (*Erysiphe graminis*), against the pathogen of glume blotch of wheat (*Leptosphaeria nodorum*), against the pathogen of spot blotch of barley (*Cochliobolus sativus*) or against the pathogen of net blotch of barley (*Pyrenophora teres*), for combating rice diseases, such as, for example, for combating rice blast (*Pyricularia oryzae*) or for combating rice stem blight (*Pellicularia sasakii*) or for combating diseases in fruit and vegetable production, such as, for example, against the pathogen of bean grey mould (*Botrytis cinerea*) or against the pathogen of apple scab (*Venturia inaequalis*) and also against true mildew fungi and rust fungi in vegetable cultivations. Moreover, the active compounds according to the invention possess a particularly broad spectrum of fungicidal activity in in vitro tests.

At suitable application rates, moreover, the active compounds according to the invention also possess a growth-regulating action in cultivated plants.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolith and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on etc. It is furthermore possible to apply the active compounds by the ultra-low-volume method or to inject the active compound preparation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

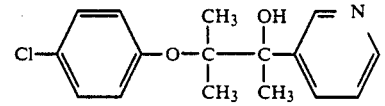

Process a 26.5 g (0.18 mol) of isopropylmagnesium bromide in 130 ml of diethyl ether are added at room temperature with stirring to 28.4 g (0.18 mol) of 3-bromopyridine in 95 ml of diethyl ether, the mixture is stirred for 30 minutes and 31.9 g (0.15 mol) of 3-methyl-3-(4-chlorophenoxy)-butan-2-one (compare, for example, EP 54,865) are then added dropwise with stirring and after completion of the addition the mixture is stirred for 4 hours at reflux temperature, cooled to 25° C. and 50 ml of water are added dropwise with ice-cooling. The mixture is brought to pH 5 to pH 6 with diluted hydrochloric acid, and the organic phase is separated off, washed using water, dried over sodium sulphate and concentrated in vacuo. The residue is purified by chromatography on silica gel (ethyl acetate/cyclohexane 3:1).

12.7 g (29% of theory) of 3-(4-chlorophenoxy)-3-methyl-2-(3-pyridyl)-butan-2-ol of melting point 140° C.–141° C. are obtained.

Example 2

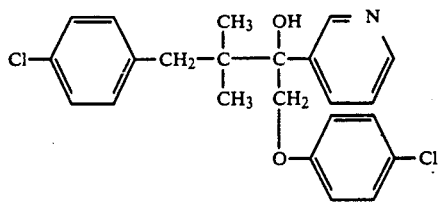

Process a 16.5 g (0.112 mol) of isopropylmagnesium bromide in 90 ml of diethyl ether are added dropwise at room temperature to 17.6 g (0.112 mol) of 3-bromopyridine in 90 ml of tetrahydrofuran and the mixture is stirred for 30 minutes after completion of the addition. 31.4 g (0.093 mol) of 1-(4-chlorophenoxy)-4-(4-chlorophenyl)-3,3-dimethyl-butan-2-one in 70 ml of diethyl ether are then added dropwise with stirring, after completion of the addition the mixture is stirred for 4 hours at reflux temperature, cooled to room temperature, 50 ml of water are added with cooling, the mixture is adjusted with dilute hydrochloric acid to pH 6–pH 7, and the organic phase is separated off, washed using water, dried over sodium sulphate and concentrated in vacuo. The residue is purified by chromatography on silica gel (ethyl acetate/cyclohexane 1:3).

10.8 g (28% of theory) of 1-(4-chlorophenoxy)-4-(4-chlorophenyl)-3,3-dimethyl-2-(3-pyridyl)-butan-2-ol of melting point 46° C.–47° C. are obtained.

PREPARATION OF THE STARTING COMPOUND

Example II-1

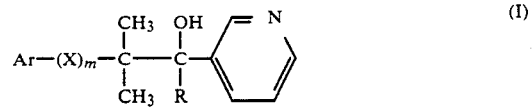

46.3 g (0.36 mol) of 4-chlorophenol and 49.7 g (0.36 mol) of potassium carbonate in 150 ml of toluene are heated for 2 hours under reflux over a water separator. 87 g (0.3 mol) of 1-bromo-4-(4-chlorophenyl)-3,3-dimethyl-butan-2-one (compare, for example, DE 3,229,273) in 150 ml of toluene are then added dropwise with stirring at 60° C., after completion of the addition the mixture is stirred for a further 5 hours at 100° C., cooled, the deposited precipitate is filtered off with suction, the filtrate is washed with dilute sodium hydroxide solution and water, and dried over sodium sulphate and the solvent is removed in vacuo.

80.7 g (80% of theory) of 1-(4-chlorophenoxy)-4-(4-chlorophenyl)-3,3-dimethylbutan-2-one are obtained as an oil, which is employed without further purification in the following reaction.

The following substituted pyridine derivatives of the general formula (I)

$$Ar-(X)_m-\underset{\underset{CH_3}{|}}{\overset{\overset{CH_3}{|}}{C}}-\underset{\underset{R}{|}}{\overset{\overset{OH}{|}}{C}}-\text{(3-pyridyl)} \quad (I)$$

are obtained in a corresponding manner and according to the general instructions for preparation:

| Example No. | Ar | —(X)$_m$— | R | Physical properties |
|---|---|---|---|---|
| 3 | F$_3$CO—C$_6$H$_4$— | —CH$_2$— | —CH$_3$ | $^1$H-NMR*: 1.73(s); 0.83(s); 0.77(s) |
| 4 | Cl—C$_6$H$_4$— | —CH$_2$— | —CH$_3$ | $^1$H-NMR*: 1.70(s); 0.83(s); 0.77(s) |
| 5 | F$_3$CS—C$_6$H$_4$— | —CH$_2$— | —CH$_3$ | $n_D^{20}$ 1.5251 |
| 6 | F—C$_6$H$_4$— | —O— | —CH$_3$ | m.p. 125° C. |
| 7 | Cl—C$_6$H$_4$— | —O—CH$_2$— | —CH$_3$ | $n_D^{20}$ 1.5471 |

-continued

| Example No. | Ar | —(X)$_m$— | R | Physical properties |
|---|---|---|---|---|
| 8 | 4-Cl-C$_6$H$_4$— | —S— | —CH$_3$ | m.p. 116° C. |
| 9 | 4-F$_3$CS-C$_6$H$_4$— | —CH$_2$— | —CH$_2$—O—C$_6$H$_4$-4-Cl | $n_D^{20}$ 1.5704 |
| 10 | C$_6$H$_5$— | —CH$_2$— | —CH$_2$—O—C$_6$H$_4$-4-Cl | m.p. 40–42° C. |
| 11 | 3,4-Cl$_2$-C$_6$H$_3$— | —CH$_2$— | —CH$_3$ | $n_D^{20}$ 1.5563 |
| 12 | 4-Cl-C$_6$H$_4$— | —S—CH$_2$— | —CH$_3$ | $n_D^{20}$ 1.5730 |
| 13 | 2-CH$_3$-C$_6$H$_4$— | —O— | —CH$_3$ | $^1$H-NMR*: |
| 14 | 4-F$_3$CO-C$_6$H$_4$— | —CH$_2$— | —CH$_2$—O—C$_6$H$_4$-4-Cl | m.p. 42–44° C. |
| 15 | 4-F-C$_6$H$_4$— | —CH$_2$— | —CH$_3$ | m.p. 126–128° C. |
| 16 | 2-Cl-C$_6$H$_4$— | —CH$_2$— | —CH$_3$ | $n_D^{20}$ 1.5592 |
| 17 | 4-CH$_3$-C$_6$H$_4$— | —CH$_2$— | —CH$_3$ | $n_D^{20}$ 1.5458 |
| 18 | 4-Br-C$_6$H$_4$— | —CH$_2$— | —CH$_3$ | $n_D^{20}$ 1.5586 |
| 19 | 2,4-Cl$_2$-C$_6$H$_3$— | —CH$_2$— | —CH$_3$ | $n_D^{20}$ 1.5715 |

-continued

| Example No. | Ar | —(X)$_m$— | R | Physical properties |
|---|---|---|---|---|
| 20 | 3-Cl-C$_6$H$_4$— | —CH$_2$— | —CH$_3$ | n$_D^{20}$ 1.5691 |
| 21 | 4-(CH$_3$)$_3$C-C$_6$H$_4$— | —S— | —CH$_3$ | m.p. 121–123° C. |
| 22 | 4-(CH$_3$)$_3$C-C$_6$H$_4$— | —O— | —CH$_3$ | m.p. 145° C. |
| 23 | 2,4-Cl$_2$-C$_6$H$_3$— | —O— | —CH$_3$ | $^1$H-NMR*: 1.85(s); 1.37(s); 1.20(s) |
| 24 | 3,4-Cl$_2$-C$_6$H$_3$— | —O— | —CH$_3$ | m.p. 172° C. |
| 25 | 2-Cl-C$_6$H$_4$— | —O— | —CH$_3$ | $^1$H-NMR*: 1.85(s); 1.40(s); 1.20(s) |
| 26 | 2,4-F$_2$-C$_6$H$_3$— | —O— | —CH$_3$ | m.p. 134° C. |
| 27 | 4-CH$_3$-C$_6$H$_4$— | —O— | —CH$_3$ | m.p. 155° C. |
| 28 | 4-(CH$_3$ON=CH)-C$_6$H$_4$— | —O— | —CH$_3$ | m.p. 122–123° C. |
| 29 | 2-Cl-4-(F$_3$CO)-C$_6$H$_3$— | —CH$_2$— | —CH$_3$ | $^1$H-NMR*: 1.72(s); 0.80(s); 0.87(s) |
| 30 | C$_6$H$_5$— | —O— | —CH$_3$ | m.p. 102° C. |
| 31 | 4-Br-C$_6$H$_4$— | —O— | —CH$_3$ | m.p. 141–143° C. |

-continued

| Example No. | Ar | —(X)$_m$— | R | Physical properties |
|---|---|---|---|---|
| 32 | 2,3-dimethylphenyl | —O— | —CH$_3$ | m.p. 151–152° C. |
| 33 | 4-bromophenyl | —S— | —CH$_3$ | m.p. 127–128° C. |
| 34 | 3-chlorophenyl | —O— | —CH$_3$ | m.p. 108° C. |
| 35 | 3,5-dichlorophenyl | —O— | —CH$_3$ | m.p. 138° C. |
| 36 | 2-fluorophenyl | —O— | —CH$_3$ | m.p. 91° C. |
| 37 | 4-biphenylyl | —O— | —CH$_3$ | m.p. 164° C. |
| 38 | 1-naphthyl | —O— | —CH$_3$ | m.p. 121° C. |
| 39 | 2-naphthyl | —O— | —CH$_3$ | m.p. 159° C. |
| 40 | 2-bromophenyl | —O— | —CH$_3$ | n$_D^{20}$ 1.5671 |
| 41 | 3-methylphenyl | —O— | —CH$_3$ | m.p. 67–69° C. |

-continued

| Example No. | Ar | —(X)$_m$— | R | Physical properties |
|---|---|---|---|---|
| 42 | 4-NC-C$_6$H$_4$— | —O—CH$_2$— | —CH$_3$ | $^1$H-NMR*: |
| 43 | 4-NC-C$_6$H$_4$— | —S—CH$_2$— | —CH$_3$ | $^1$H-NMR*: |
| 44 | 2-Cl-4-CH$_3$-C$_6$H$_3$— | —O— | —CH$_3$ | m.p. 145° C. |
| 45 | 4-CH$_3$S-C$_6$H$_4$— | —O— | —CH$_3$ | m.p. 124° C. |
| 46 | 4-NC-C$_6$H$_4$— | —O— | —CH$_3$ | m.p. 156° C. |
| 47 | 4-F$_3$CO-C$_6$H$_4$— | —O— | CH$_3$ | mp. 118° C. |
| 48 | 4-Br-C$_6$H$_4$— | —O—CH$_2$— | CH$_3$ | mp. 109–113° C. |
| 49 | 3,5-(CH$_3$)$_2$-4-Cl-C$_6$H$_2$— | —O— | CH$_3$ | mp. 173° C. |
| 50 | 4-Cl-3-CH$_3$-C$_6$H$_3$— | —O— | CH$_3$ | mp. 145° C. |
| 51 | 4-CH$_3$S-3-CH$_3$-C$_6$H$_3$— | —O— | CH$_3$ | mp. 115° C. |
| 52 | 3-(CH$_3$)$_2$CHO-C$_6$H$_4$— | —O— | CH$_3$ | oil |

-continued

| Example No. | Ar | —(X)$_m$— | R | Physical properties |
|---|---|---|---|---|
| 53 | CH$_3$O—C$_6$H$_4$— | —O— | CH$_3$ | mp. 145° C. |
| 54 | cyclohexyl-C$_6$H$_4$— | —O— | CH$_3$ | mp. 103° C. |
| 55 | 4-Cl-2-CH$_3$-C$_6$H$_3$— | —O— | CH$_3$ | n$_D^{20}$ 1.5491 |
| 56 | 3,5-(CH$_3$)$_2$-C$_6$H$_3$— | —O— | CH$_3$ | mp. 106° C. |
| 57 | (C$_6$H$_5$)(CH$_3$)$_2$C—C$_6$H$_4$— | —O— | CH$_3$ | n$_D^{20}$ 1.5723 |
| 58 | C$_6$H$_5$—O—C$_6$H$_4$— | —O— | CH$_3$ | mp. 129–131° C. |
| 59 | C$_6$H$_5$—CH$_2$—O—C$_6$H$_4$— | —O— | CH$_3$ | mp. 103–105° C. |
| 60 | (CH$_3$)$_3$C—CH$_2$—C(CH$_3$)$_2$—C$_6$H$_4$— | —O— | CH$_3$ | mp. 131–133° C. |
| 61 | 6-Br-naphth-2-yl | —O— | CH$_3$ | mp. 123° C. |
| 62 | 3-CH$_3$-biphenyl-4-yl | —O— | CH$_3$ | n$_D^{20}$ 1.5961 |

*The $^1$H-NMR spectra were recorded in deuterochloroform (CDCl$_3$) using tetramethylsilane (TMS) as the internal standard. The chemical shift is given as the δ-value in ppm.

USE EXAMPLES

The compounds shown below were employed as comparison substances in the following use examples:

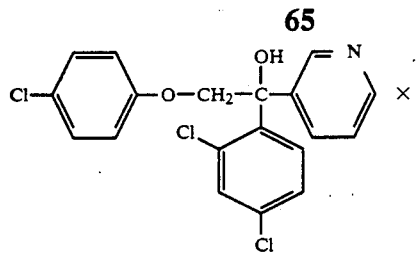 (A)

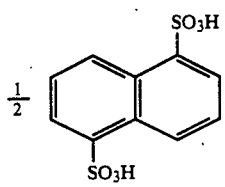 ½

2-(4-Chlorophenoxy)-1-(2,4-dichlorophenyl)-1-(3-pyridyl)ethanol naphthalene disulphonate.

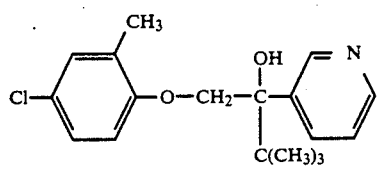 (B)

1-(4-Chloro-2-methylphenoxy)-3,3-dimethyl-2-(3-pyridyl)-2-butanol

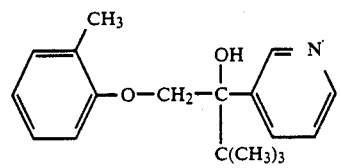 (C)

3,3-Dimethyl-1-(2-methylphenoxy)-2-(3-pyridyl)-2-butanol

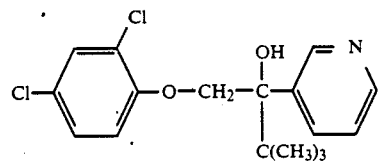 (D)

1-(2,4-Dichlorophenoxy)-3,3-dimethyl-2-(3-pyridyl)-2-butanol (all known from EP 1,399).

EXAMPLE A

Botrytis test (bean)/protective
Solvent: 4.7 parts by weight of acetone
Emulsifier: 0.3 parts by weight alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, a clearly superior activity compared with the prior art is shown, for example, by the compounds according to the Preparation Examples 1, 3, 5, 7, 8 and 15.

EXAMPLE B

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compound according to Preparation Example 3.

EXAMPLE C

Pyricularia test (rice)/protective
Solvent: 12.5 parts by weight of acetone
Emulsifier: 0.3 parts by weight of alkylarylpolyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the Preparation Examples 1, 3, 4, 10, 18 and 19.

EXAMPLE D

Pellicularia test (rice)
Solvent: 12.5 parts by weight of acetone
Emulsifier: 0.3 parts by weight of alkylarylpolyglycol ether To produce a suitable preparation of active compound, 1 part by weight of active compound is mixed with the stated amount of solvent, and the concentrate is diluted with water and the stated amount of emulsifier to the desired concentration.

To test for activity, young rice plants in the 3-to 4-leaf stage are sprayed until dripping wet. The plants remain in the greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the Preparation Examples 1 and 10.

EXAMPLE E

Pyrenophora teres-test (barley)/protective
Solvent: 100 parts by weight of dimethylformamide
Emulsifier: 0.25 parts by weight of alkylaryl polyglcol ether To produce a suitable preparation of active compound, 1 part by weight of active compound is mixed with the stated amounts of solvent and emulsifier, and the concentrat is diluted with water to desired concentration.

To test for protective activity, young plants are sprayed with the preparation of active compound until dew-moist. After the spray coating has dried on, the plants are sprayed with a conidia suspension of Pyrenophora teres.

The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the Preparation Examples 3, 4, 5, 8, 15, 25, 26, 29, 28, 47, 49, 50, 51 and 53.

EXAMPLE F

Cochliobolus sativus-test (barley)/protective
Solvent: 100 parts by weight of dimethylformamide
Emulsifier: 0.25 parts by weight of alkylaryl polyglcol ether To produce a suitable preparation of active compound, 1 part by weight of active compound is mixed with the stated amount of solvent and emulsifier, and the concentrate is diluted with water to desired concentration.

To test for protective activity, young plants are sprayed with the preparation of active compound until dew-moist. After the spray coating has dried on, the plants are sprayed with a conidia suspension of Cochliobolus sativus.

The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the Preparation Examples 3, 4, 5, 1, 15, 17, 31, 47, 39, 41, 49, 50, 51, 52 and 53.

EXAMPLE G

Leptosphaeria nodorum-test (wheat)/protective
Solvent: 100 parts by weight of dimethylformamide
Emulsifier: 0.25 parts by weight of alkylaryl polyglcol ether To produce a suitable preparation of active compound, 1 part by weight of active compound is mixed with the stated amounts of solvent and emulsifier, and the concentrate is diluted with water to desired concentration.

To test for protective activity, young plants are sprayed with the preparation of active compound until dew-moist. After the spray coating has dried on, the plants are sprayed with a spore suspension of Leptosphaeria nodorum.

The plants then remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compounds according to the Preparation Examples 3, 4, 5, 1, 8, 17, 20, 26, 29, 47, 39 and 48.

EXAMPLE H

Puccinia-test (wheat)/protective
Sovent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist.

The plants then remain in an incubation cabin at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the Preparation Examples 9, 10, 11, 2, 14, 26, 47 and 56.

It will be appreciated that the instant specification and claims are set forth by way of illustration and not limitation, and that various modifications and changes may be made without departing from the spirit and scope of the present invention.

We claim:

1. A substituted pyridine derivative of the formula

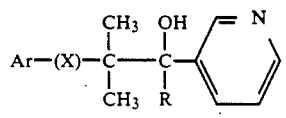

in which
Ar stands for phenyl which is monosubstituted by a substituent selected from the group consisting of cyano, nitro, methylthio, ethylthio, trifluoromethylthio, difluoromethylthio, fluoromethylthio, difluorochloromethylthio, dichlorofluoromethylthio, difluoroethylthio, difluorobromomethylthio, trichloromethylthio, trifluoroethylhio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, dichlorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, and phenyl or phenoxy which are in each case optionally monosubstituted, disubstituted or trisubstituted by fluorine or chlorine or by phenylalkyl or pohenylalkyloxy with 1 to 4 carbon atoms in straight-chain or branched alkyl or alkoxy part or cycloalkyl with 3 to 6 carbon atoms or by alkyl with 1 to 8 carbon atoms straight-chain or branched; or for phenyl which is mono- to trisubstituted identically or differently by fluorine, chlorine, bromine, methyl, ethyl, n- or i-propyl, n-, i-, s- or t-butyl, methoxy, ethoxy, n- or i-propoxy, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, methylthio, ethylthio, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorodichloroethoxy, difluorotrichloroethoxy, or pentachloroethoxy, or stands for α-naphthyl or β-naphthyl which are optionally substituted by bromine;

X is selected from the group consisting of O, S, SO and SO₂, and

R stands for methyl, ethyl, n- or i-propyl, n-, i-, s- or t-butyl, allyl, propargyl, methoxymethyl, methylthiomethyl, cyclopropyl, chlorophenoxymethyl or chlorophenylthiomethyl, or a plant-compatible acid or metal salt addition product thereof.

2. A substituted pyridine derivative or addition product according to claim 1, in which X stands for oxygen, and sulphur.

3. A compound according to claim 1, wherein such compound is 3-(4-bromophenoxy)-3-methyl-2-(3-pyridyl)-butan-2-ol of the formula

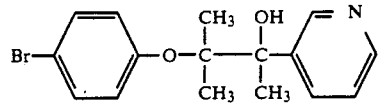

or a plant-compatible acid or metal salt addition product thereof.

4. A compound according to claim 1, wherein such compound is 3-(4-biphenyloxy)-3-methyl-2-(3-pyridyl)-butan-2-ol of the formula

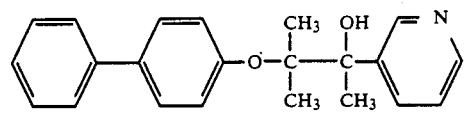

or a plant-compatible acid or metal salt addition product thereof.

5. A compound according to claim 1, wherein such compound is 3-(β-naphthyloxy)-3-methyl-2-(3-pyridyl)-butan-2-ol of the formula

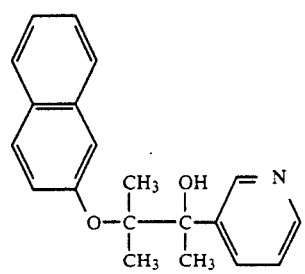

or a plant compatible acid or metal salt addition product thereof.

6. A compound according to claim 1, wherein such compound is 3-(4-trifluoromethoxyphenoxy)-3-methyl-2-(3-pyridyl)-butan-2-ol of the formula

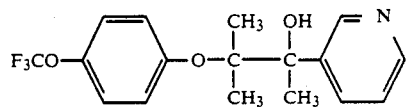

or a plant compatible acid or metal salt addition product thereof.

7. A fungicidal composition comprising a fungicidally effective amount of a compound or addition product according to claim 1 and a diluent.

8. A method of combating fungi which comprises applying to such fungi or to a fungus habitat a fungicidally effective amount of a compound or addition product according to claim 1.

9. The method according to claim 8, wherein such compound is 3-(4-bromophenoxy)-3-methyl-2-(3-pyridyl)-butan-2-ol,
3-(4-biphenyloxy)-3-methyl-2-(3-pyridyl)-butan-2-ol,
3-(β-naphthyloxy)-3-methyl-2-(3-pyridyl)-butan-2-ol,
3-(4-trifluoromethoxyphenoxy)-3-methyl-2-(3-pyridyl)-butan-2-ol.

* * * * *

UNITED STATES PATENT AND TRADEMARK OFFICE
CERTIFICATE OF CORRECTION

PATENT NO. : 5,047,544

DATED : September 10, 1991

INVENTOR(S) : Elbe et al.

It is certified that error appears in the above-identified patent and that said Letters Patent is hereby corrected as shown below:

Col. 69, line 6    Delete " trifluoroethylhio " and substitute -- trifluoroethylthio --

Col. 69, line 24   Delete " pohenylalkyloxy " and substitute --phenylalkoxy --

Col. 70, line 62   After " 2-ol, " insert -- or --

Signed and Sealed this

Third Day of August, 1993

Attest:

MICHAEL K. KIRK

*Attesting Officer*    Acting Commissioner of Patents and Trademarks